United States Patent [19]

Lesmann et al.

[11] Patent Number: 5,534,624
[45] Date of Patent: Jul. 9, 1996

[54] 1,3,5-TRIAZINE-2,4,6-TRIS-ALKYLAMINOCARBOXYLIC ACID AMINO ESTERS, BIOCIDAL AGENTS CONTAINING SUCH ESTERS, AND METHODS OF PREPARING THEM

[75] Inventors: Jörg Lesmann; Hermann G. Schäfer, both of Hamburg, Germany

[73] Assignee: CG-Chemie GmbH, Hamburg, Germany

[21] Appl. No.: 244,114
[22] PCT Filed: Sep. 29, 1992
[86] PCT No.: PCT/EP92/02249
§ 371 Date: May 19, 1994
§ 102(e) Date: May 19, 1994
[87] PCT Pub. No.: WO93/10105
PCT Pub. Date: May 27, 1993

[30] Foreign Application Priority Data

Nov. 19, 1991 [DE] Germany ............... 41 38 089.4

[51] Int. Cl.⁶ ................................. C07D 251/54
[52] U.S. Cl. ............................... 544/196; 544/200
[58] Field of Search ................. 514/245, 256, 514/345, 558, 559, 561, 562, 563; 544/196, 200

[56] References Cited

U.S. PATENT DOCUMENTS 4,402,907   9/1983   Clark ................................ 544/196
4,877,552  10/1989   Haring .............................. 544/196

FOREIGN PATENT DOCUMENTS 0046139  2/1982  European Pat. Off. .
0262086  3/1989  European Pat. Off. .

OTHER PUBLICATIONS

Nestler, H., et al., "Preparation of N-(1,3,5-triazinyl)amino acid derivatives", *Chemical Abstracts*, vol. 60, Abstract No. 4145e, Col. 4144 (1964).

*Chemical Abstracts, Registry Handbook—Number Section*, (1986) Columbus US, p. 2992, CAS RN 103479-85-2.

*Chemical Abstracts, Registry Handbook—Number Section*, (1982) Columbus US, p. 156, CAS RN 80584-91-4.

*Chemical Abstracts, Registry Handbook—Number Section*, (1982) Columbus US, p. 156, CAS RN 80584-92-5.

*Chemical Abstracts, Registry Handbook—Number Section*, (1991) Columbus US, p. 3274, CAS RN 135043-68-4 & 135043-69-5.

*Primary Examiner*—Yogendra N. Gupta
*Attorney, Agent, or Firm*—Walter H. Dreger

[57] ABSTRACT

1,3,5-Triazine-2,4,6-tris-alkylaminocarboxylic acid amino esters of the general formula (I): 1,3,5-triazine-2,4,6-tris [NH—$(CH_2)_n$—CO—O—$R^1$], in which $R^1$ denotes the radical of an alkanolamine, can be employed as biocidal or biostatic compounds in aqueous systems, in particular in cooling lubricants.

3 Claims, No Drawings

1,3,5-TRIAZINE-2,4,6-TRIS-ALKYLAMINOCARBOXYLIC ACID AMINO ESTERS, BIOCIDAL AGENTS CONTAINING SUCH ESTERS, AND METHODS OF PREPARING THEM

The invention relates to 1,3,5-triazine-2,4,6-tris-alkylaminocarboxylic acid amino esters, biocidal and biostatic agents containing such amino esters and methods of preparing them. The abovementioned compounds are called "amino esters of the invention" below.

The triazinetricarboxylic acids on which the amino esters of the invention are based, that is to say the 2,4,6-tris(omega-carboxyalkylamino)-1,3,5-triazines, called 1,3,5-triazine-2,4,6-tris-alkylaminocarboxylic acids below, are described in J. Prakt. Chemie, 23 (1963), pages 173 to 185, and in EP-B 0 046 139. EP-B 0 046 139 furthermore relates to the use of the triazinetricarboxylic acids mentioned and alkali metal and mono-, di- or triethanolammonium salts thereof as corrosion inhibitors in aqueous systems. EP-B 0 046 139 furthermore describes the mono-, di- and triethanolammonium salts of these triazinetricarboxylic acids, which can be employed as corrosion inhibitors in aqueous systems; an analogous use of these compounds in aqueous systems, for example cooling liquids, cooling lubricants, paints or cleaning agents, is disclosed in EP-A 0 262 086.

Biocidal or biostatic agents have to be added to aqueous systems of the abovementioned type for prevention of attack by bacteria, yeasts and/or fungi. Halogen-containing compounds and, for example, boric acid and reaction products of boric acid with alkanolamines have been used to date as agents which are suitable for this purpose, see Ullmanns Encyklopädie der technischen Chemie (Ullmann's Encyclopaedia of Industrial Chemistry), 4th edition, Volume 8, Verlag Chemie, Weinheim 1974, pages 653–655. In other cases, formaldehyde or formaldehyde derivatives have been added as the biocide. However, for various reasons, halogen-containing compounds, boric acid and boric acid derivatives and also formaldehyde and derivatives thereof are undesirable. There is therefore an increasing need for biocidal agents which can be used in aqueous systems and are free from halogen-containing compounds, formaldehyde, formaldehyde derivatives, boric acid or boric acid derivatives.

It has now been found that the amino esters of the invention display excellent biocidal or biostatic properties when used in aqueous systems of the above-mentioned type even in low concentrations.

The invention accordingly relates to 1,3,5-triazine-2,4,6-tris-alkylaminocarboxylic acid amino esters of the general formula

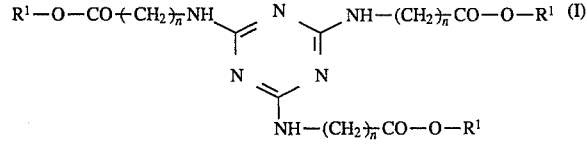

in which n denotes a number in the range from 4 to 11 and $R^1$ denotes a radical of an alkanolamine of the general formula

in which at least one of the groups $R^2$ is a) a hydroxyalkyl group having 2 to 4 carbon atoms, b) a hydroxyalkyl-oxyalkylene group having 4 to 6 carbon atoms or c) a dihydroxyalkyl group having 3 to 6 carbon atoms and, if less than three of the groups $R^2$ have the above meaning, the other groups $R^2$ are hydrogen.

A preferred embodiment of the invention relates to amino esters of the general formula I in which n denotes the number 5.

The alkanolamines of the general formula II contain primary, secondary or tertiary amino groups and free hydroxyl groups. In the reaction of alkanolamines containing primary or secondary amino groups with carboxylic acids, both amides and esters which are in equilibrium with one another can be formed, see "Surfactants in Consumer Products", editor J. Falbe, Springer-Verlag, Heidelberg 1987, page 96. For clarity, the reaction products of 1,3,5-triazine-2,4,6-tris-alkylaminocarboxylic acids with alkanolamines to give compounds of the general formula I in which $R^1$ is the radical of an alkanolamine of the general formula II are shown here only as amino esters. However, it can readily be seen by the expert that the corresponding alkanolamides also fall under the 1,3,5-triazine-2,4,6-tris-alkylcarboxylic acid derivatives thus defined.

Typical examples of hydroxyalkyl groups having 2 to 4 carbon atoms which can form the group $R^2$ are 2-hydroxyethyl, 1-methyl-2-hydroxyethyl, 2-hydroxypropyl, 3-hydroxypropyl, 2-hydroxybutyl, 4-hydroxybutyl and 2-methyl-2-hydroxypropyl groups; typical examples of hydroxyalkyl-oxyalkylene groups having in each case 2 to 4 carbon atoms in the hydroxyalkyl and oxyalkylene radical are hydroxyethyl-oxyethylene, hydroxypropyloxyethylene, hydroxyethyl-diethyleneoxy, hydroxyethyloxypropylene and hydroxypropyl-oxypropylene groups, and typical examples of dihydroxyalkyl groups having 3 to 6 carbon atoms are 2,3-dihydroxypropyl, 3,4-dihydroxybutyl, 1,3-dihydroxypropyl and 1,3-dihydroxy-2-methyl- or -ethyl-propyl groups; and furthermore also hydroxyethyl-, hydroxypropyl- and hydroxybutyl-oxybutylene groups.

Compounds of the general formula I in which $R^1$ denotes a radical of an alkanolamine of the general formula II are obtainable by reaction of 1,3,5-triazine-2,4,6-tris-alkylaminocarboxylic acids of the general formula

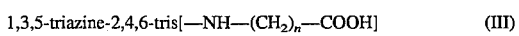

in which n is as defined above, with alkanolamines of the general formula II by processes which are known per se.

For many intended uses, it is not necessary for the amino esters of the invention to be isolated in bulk. Rather, it is sufficient for the amino esters of the invention to be prepared "in situ", for example in an excess of the alkanolamines of the general formula II, and if appropriate for the excess of alkanolamines to be neutralized with suitable acids which do not interfere with or under certain circumstances even promote the desired intended use.

The reaction with a molar excess of the alkanolamines, based on the 1,3,5-triazine-2,4,6-tris-alkylaminocarboxylic acids, is therefore preferred. The unreacted portion of the alkanolamines can be reacted with organic acids chosen from the group formed by straight-chain or branched, saturated or unsaturated fatty acids having 5 to 22 carbon atoms to establish a pH of 4.5 to 9.5. Examples of the fatty acids mentioned are pentanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, nonadecanoic acid, eicosanoic acid, heneicosanoic acid, docosanoic acid, 10-undecenoic acid, 9c-dodecenoic acid, 9c-tetradecenoic acid, 9c-hexadecenoic acid, 6c-octadecenoic acid, 6t-octadecenoic acid, 9c-octadecenoic acid, 9t-octadecenoic acid, 9c,12c-octadecadienoic acid, 9t,12t-octadecadienoic acid, 9c,12c,15c-octadecatrienoic acid, 9c,11t,13t-octadecatrienoic acid, 9c-eicosenoic acid, 5,8,11,14-eicosatetraenoic acid, 13c-docosenoic acid, 13t-docosenoic acid, 4,8,12,15,19-docosapentaenoic acid, 12-hydroxy-octadecanoic acid and 12-hydroxy-9c-octadecenoic acid, c indicating a cis double bond and t a trans double bond, and technical-grade mixtures thereof. Fatty acids and fatty acid mixtures which are obtainable from renewable raw materials, in particular vegetable and/or animal fats and oils, for example caproic, caprylic, capric, lauric, myristic, palmitic, stearic, oleic, ricinoleic, linoleic, erucic and behenic acid, are also particularly suitable.

The unreacted portion of the alkanolamines is preferably reacted with straight-chain or branched, saturated or unsaturated fatty acids having 5 to 11 carbon atoms. If no stable solutions or emulsions are obtained in this manner, straight-chain or branched, saturated or unsaturated fatty acids having 12 to 22 carbon atoms can additionally be used to establish the desired hydrophilic/hydrophobic balance.

Those amino esters of the general formula I which contain no secondary or tertiary amino functions are preferred. Secondary alkanolamines can form undesirable stable nitrosamines with nitrite ions. Under certain circumstances, tertiary alkanolamines can form secondary alkanolamines by dealkylation. In contrast, primary alkanolamines as a rule do not form stable nitrosamines, but rather are used as trapping agents for nitrite ions because of the rapid dissociation of the nitrosamines intermediately formed. If amino esters of the general formula I which are derived from secondary alkanolamines nevertheless are to be employed, it is preferable to use a mixture of compounds derived from primary and secondary alkanolamines, since formation of the unstable primary nitrosamines then takes place more rapidly than that of the secondary nitrosamines.

According to another aspect, the invention thus relates to amino esters of the general formula I which are free from secondary or tertiary amino functions and thus cannot form stable nitroso compounds or which, if the analogous compounds of the general formula I containing secondary or tertiary amino functions are present at the same time, prevent the formation of stable nitroso compounds.

Biocidal or biostatic mixtures of monocarboxylic acid alkanolamides and amino esters of the general formula I and if appropriate alkanolammonium salts of the monocarboxylic acids and/or of the 1,3,5-triazine-2,4,6-tris-alkylaminocarboxylic acids can also be prepared by the process of the invention.

The abovementioned biocidal and biostatic mixtures can be prepared by mixing the individual components. However, they are expediently prepared by preparing the alkanolamides in situ from the monocarboxylic acids and the 1,3,5-triazine-tris-alkylaminocarboxylic acids of the general formula III, in which n is as defined above, with alkanolamines of the general formula II, in which $R^2$ is as defined above, preferably in an excess of the alkanolamines.

Primary alkanolamines or mixtures of primary and secondary alkanolamines are preferably used.

Preferably, 10 to 50 mol, in particular 10 to 30 mol, of the alkanolamines of the general formula II and 0.5 to 5 mol of the monocarboxylic acids are reacted per mol of the 1,3,5-triazine-2,4,6-tris-alkylaminocarboxylic acids.

The amino esters of the invention are prepared at a temperature in the range from 100° to 180°, in particular 130° to 180° C.

Straight-chain or branched, saturated or unsaturated fatty acids having 3 to 22, in particular 12 to 22, carbon atoms are preferably used as the monocarboxylic acids and are reacted in a first stage with the alkanolamines to give the corresponding amino esters or alkanolamides, which is followed by addition and reaction of the 1,3,5-triazine-2,4,6-tris-alkylaminocarboxylic acids with the excess of alkanolamines present to give the amino esters of the invention in a second stage. This reaction can also be carried out in a different sequence or in a single stage, but under certain circumstances less pronounced biocidal or biostatic properties of the mixture are then obtained.

Monocarboxylic acids which are furthermore used are preferably ether-carboxylic acids of the general formula

$$R^3\text{-}(O\text{---}C_mH_{2m})_q\text{---}O\text{---}CH_2\text{---}COOH \qquad (III)$$

in which $R^3$ denotes a straight-chain or branched alkyl or alkenyl group having 9 to 18 carbon atoms, m denotes the number 2 and/or 3 and q denotes a number in the range from 0 to 100, preferably from 0 to 20.

The reaction here can be carried out in any desired sequence, but also in a single stage.

Monocarboxylic acids which are likewise used are preferably arylsulphonamidocarboxylic acids of the general formula

$$(R^4)\text{aryl}\text{---}SO_2\text{---}N(R^5)\text{---}R^6\text{---}COOH \qquad (Va)$$

in which $R^4$ denotes hydrogen or a methyl or a ethyl group or several groups, $R^5$ denotes hydrogen or a methyl, ethyl, beta-cyanoethyl or hydroxymethyl group, $R^6$ denotes an alkylene group having 4 to 6 carbon atoms and aryl denotes a phenyl, naphthyl or anthracenyl radical, alkylsulphonamidocarboxylic acids of the general formula

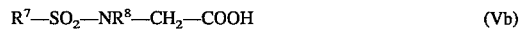

$$R^7\text{---}SO_2\text{---}NR^8\text{---}CH_2\text{---}COOH \qquad (Vb)$$

in which $R^7$ denotes a straight-chain or branched alkyl group having 12 to 22 carbon atoms and $R^8$ denotes hydrogen or the group ---$CH_2$---COOH, and/or half-esters or half-amides of the general formula Vc

$$R^9\text{---}OOC\text{---}R^{10}\text{---}COOH \qquad (Vc)$$

in which $R^9$ is the radical of an alkanolamine of the general formula II and $R^{10}$ is an o-phenylene, vinylene or 1,2-ethylene radical. Here also, the reaction can be carried out in any desired sequence, but also in a single stage. It has not yet been possible to determine whether the sulphonamidocarboxylic acids of the general formula Va or Vb are reacted with the alkanolamines of the general formula II to give sulphonamidocarboxylic acid aminoalkyl esters, to give sulphonamidocarboxylic acid alkanolamides or to give mixtures thereof. For simplicity, these reaction products are always called alkanolamides here. The abovementioned sulphonamidocarboxylic acids are known, for example, from DE-C 28 40 112 and DE-A 33 04 164.

Excess alkanolamine contained in the resulting reaction mixture can then be reacted with fatty acids having 3 to 22, preferably 3 to 11, carbon atoms, ethercarboxylic acids of the general formula IV, in which $R^3$, m and q are as defined above, and/or aryl- or alkyl-sulphonamidocarboxylic acids of the general formula Va or Vb, in which $R^4$, $R^5$, $R^6$, $R^7$, $R^8$ and $R^9$ are as defined above, to establish a pH in the range from 4.5 to 9.5.

It is preferable to carry out all the reactions such that the reaction mixture is always kept liquid. This is achieved, for example, with the preferred large excess of alkanolamines.

Finally, the fungicides described below can also be added to the reaction mixture after the reaction, preferably in an amount of 1 part by weight of fungicides per 10 to 100 parts by weight of the amino esters of the general formula I, in which $R^1$ and n are as defined above, contained in the biocidal or biostatic mixture.

An excess of alkanolamines present after the reaction described above is completely or partly neutralized, as mentioned above, to establish a suitable pH range and with the formation of further contents of alkanolamides or alkanolammonium salts.

Examples of straight-chain or branched, saturated or unsaturated fatty acids having 3 to 22 carbon atoms are propanoic acid, the abovementioned fatty acids having 5 to 22 carbon atoms and technical-grade mixtures thereof. The reaction products of the alkanolamines with the monocarboxylic acids furthermore can serve as anti-corrosion agents in the aqueous systems.

Preferred examples of alkanolamines of the general formula II, in which $R^2$ is as defined above, which can be used according to the invention are mono-, di- and triethanolamine, mono-, di- and tripropanolamine, mono-, di- and triisopropanolamine, 2-amino-1-butanol, 2-(2'-aminoethoxy)-ethanol, 2-amino-2-methyl-1-propanol and 2-amino-2-ethyl-1,3-propanediol; as already mentioned, alkanolamines having primary amino groups or mixtures thereof with alkanolamines having secondary amino groups are particularly preferred.

Secondary alkanolamines which, in addition to having a single hydroxyalkyl, hydroxyalkyl-oxyalkylene or dihydroxyalkyl group according to the definitions given above for $R^2$, are substituted by an alkyl group having 1 to 6 carbon atoms, for example methyl, ethyl, n-propyl, i-propyl, n-butyl, i-butyl, pentyl, cyclopentyl, hexyl or cyclohexyl, furthermore are also preferred.

Such secondary monoalkanol-monoalkylamines are commercially available; typical representatives are methyl-hydroxyethyl-amine, n-butyl-hydroxyethylamine and cyclohexyl-hydroxyethyl-amine and the correspondingly substituted hydroxypropyl derivatives. Some of the compounds of the general formula I derived from these monoalkanolmonoalkylamines have pronounced fungicidal properties which render the addition of other fungicides to improve the biostatic properties superfluous.

Examples of alkylene groups having 4 to 6 carbon atoms which can form the radical $R^6$ are butylene, pentylene, hexylene, 2-methyl-propylene, 2-methyl-butylene, 3-methyl-butylene, 2,2-dimethylpropylene and 2,2-dimethylbutylene groups.

Examples of alkyl groups having 12 to 22 carbon atoms which can form the radical $R^7$ are the dodecyl, tridecyl, tetradecyl, pentadecyl, hexadecyl, heptadecyl, octadecyl, nonadecyl, eicosyl, heneicosyl and docosyl group.

The biocidal or biostatic action of the amino esters of the general formula I used according to the invention extends to bacteria, yeasts and fungi. The limits between a biocidal and a biostatic action merge here. Either the biocidal (germ-destroying) or the biostatic (growth inhibiting) action predominates, depending on the amount used and the duration of the action. If a fungicide is also used in addition to the amino esters of the invention, synergistic effects occur, that is to say the actions mutually intensify each other. Examples of fungicides are pyrithione and derivatives thereof, N-alkyl- or N-aryl-, in particular N-cyclohexyldiazenium dioxide salts, for example with potassium, aluminium, tin or copper as the metal component (Ullmanns Encyklopädie der technischen Chemie (Ullmann's Encyclopaedia of Industrial Chemistry), 4th edition, Volume 17, Verlag Chemie, Weinheim 1979, page 369), phenols, cresols, 1,2-benzisothiazolin-3-one and derivatives thereof and also 2-methyl- and 2-octyl-4-isothiazolin-3one, halogen-free compounds being preferred. Fungicides which are water-soluble and stable to alkali furthermore are preferably employed.

According to another preferred embodiment of the invention, pyrithione or derivatives thereof and/or N-alkyl- or N-aryl-, in particular N-cyclohexyl-diazenium dioxide salts, for example with potassium, aluminium, tin or copper as the metal component, are used as the fungicides. Pyrithione is the abbreviated name for 2-pyridinethiol 1-oxide, which is in tautomeric equilibrium with 1-hydroxy-2-pyridinethione. Possible derivatives of pyrithione are the ammonium, sodium, magnesium and zinc salts and 2,2'-dithiobis(pyridine 1,1'-dioxide), the disulphide of pyrithione. Under certain circumstances, the anion of pyrithione can be precipitated by heavy metals. In contrast, the abovementioned N-alkyl- and N-aryl-diazenium dioxide salts also have complexing properties, in addition to fungicidal properties. A mixture of pyrithione or derivatives thereof and the abovementioned N-alkyldiazenium dioxide salts is therefore preferably used. However, it is also possible to employ only pyrithione or derivatives thereof, the fungicidal action being retained in the absence of significant amounts of heavy metals. Since combinations of the fungicides mentioned with the amino esters according to the invention display synergistic effects, very small amounts thereof are sufficient for the use according to the invention in aqueous systems.

The aqueous systems which can be prepared according to the invention comprise 0.05 to 0.40% by weight of the amino esters of the general formula I and 0.0001 to 0.2% by weight, preferably 0,001 to 0.1, in particular 0.001 to 0.02% by weight of fungicides, based on the total formulation.

Uses in virtually any desired aqueous or water-containing systems are possible, for example in metalworking liquids, coolants for cooling circulations, cleaning agents, hydraulic fluids, cosmetics and paints. For use in cosmetics, these are preferably brought to a pH in the range from 4.5 to 7.0 by the process described above. In contrast, cooling lubricants are preferably brought to a pH in the range from 7.5 to 9.5.

The amino esters of the general formula I are used in particular in cooling lubricants.

Cooling lubricants are aqueous liquids which are used for cooling and lubrication, for example, during drilling, grinding, milling, turning, cutting, sawing, abrading and thread cutting or during rolling or drawing of metals. These can be classified into three groups, according to the mineral oil content:

a) synthetic cooling lubricants which are free from mineral oil, b) semi-synthetic cooling lubricants which comprise about 10 to 60% by weight of mineral oil and c) cooling lubricants which comprise about 60 to 80% of mineral oil. mineral oil.

The cooling lubricant furthermore can comprise polyglycols. Instead of mineral oils, it is also possible to use naturally occurring or synthetic fatty acid esters, for example rape oil or ester oils.

Further additives, such as corrosion inhibitors, copper passivators, antiwear agents, emulsifiers, carriers, precipitating agents, oxygen-trapping agents, complexing agents or foam prevention agents, can be added to all three types of cooling lubricants.

Examples of corrosion inhibitors are organic acids and salts and esters thereof, for example benzoic acid, p-tert-butylbenzoic acid, disodium sebacate, triethanolamine laurate, isononanoic acid, the triethanolamine salt of p-toluenesulphonamidocaproic acid, sodium N-lauroylsarcosinate or nonylphenoxyacetic acid, or polycarboxylic acids; nitrogen-containing substances, for example fatty acid alkanolamides, imidazolines, oxazolines, triazoles, triethanolamine, fatty amines, N-acylsarcosines or inorganic nitrites or nitrates; phosphorus-containing substances, for example amine phosphates, phosphonic acids, phosphonates, phosphonocarboxylic acids, phosphinocarboxylic acids or inorganic phosphates, such as $NaH_2PO_4$, and sulphur-containing substances, for example salts of petroleumsulphonates or alkylbenzenesulphonates, or heterocyclic compounds which contain one sulphur atom or more in the ring.

Copper passivators which can be used are, for example, benzotriazoles, methylene-bis-benzotriazoles, such as sodium-2-mercaptobenzotriazole, thiadiazoles, for example 2,5-dimercapto-1,3,4-thiadiazole derivatives, or tolyltriazoles.

Antiwear agents can be AW(antiwear) or EP(extreme pressure) additives, for example substances containing sulphur, phosphorus or halogen, such as sulphurated fats and olefins, tritolyl phosphate and mono- and diesters of phosphoric acid, addition products of ethylene oxide and/or propylene oxide with polyhydroxy compounds, which are optionally partly esterified with fatty acids, chloroparaffins or ethoxylated phosphate esters, chlorine-free compounds being preferred.

Examples of emulsifiers are ether-carboxylic acids, fatty acid alkanolamides, sodium petroleum-sulphonates, mono- or diesters or -ethers of polyethylene glycols, polypropylene glycols or mixed polyethylene/polypropylene glycols or fatty acid soaps.

Carriers which can be used are, for example, poly-(meth)acrylic acid and its salts, hydrolysed polyacrylonitrile, polyacrylamide and copolymers thereof, ligninsulphonic acid and salts thereof, starch and starch derivatives, cellulose, alkylphosphonic acids, 1-amino-alkyl-1,1-diphosphonic acids and their salts, polymaleic acids and other polycarboxylic acids, ester oils, naturally occurring or synthetic fatty acid esters, for example rape oil, or alkali metal phosphates.

Examples of precipitating agents are alkali metal phosphates or alkali metal carbonates.

Examples of oxygen-trapping agents are alkali metal sulphates, morpholine and hydrazine.

The amino esters of the formula I according to the invention themselves have complexing properties. However, it is also possible to add other complexing agents, for example phosphonic acid derivatives, nitrilotriacetic acid or ethylenediamine-tetraacetic acid and salts thereof. Furthermore, the N-alkyl- and N-aryldiazenium dioxide salts optionally to be employed as fungicides also have complexing properties, to which reference has already been made.

Examples of foam prevention agents are distearylsebacic acid diamide, distearyladipic acid diamide or ethylene oxide and/or propylene oxide addition products of such amides, fatty alcohols and ethylene oxide and/or propylene oxide addition products thereof, naturally occurring and synthetic waxes, silicone compounds, silicic acid derivatives and pyrogenic silicon dioxide.

Typical cooling lubricants in the context of the invention are, for example, those which comprise a) amino esters of the general formula I, b) fungicides, c) water, d) if appropriate mineral oil, e) if appropriate emulsifiers and/or further auxiliaries, f) if appropriate corrosion inhibitors, the lubricants comprising the amino esters in an amount of 0.05 to 0.40% by weight and the fungicides in an amount of 0.0001 to 0.2% by weight, preferably 0.001 to 0.1, in particular 0.001 to 0.02% by weight, based on the total amount of cooling lubricant.

Cooling lubricants which comprise, as emulsifiers and/or further auxiliaries, a) ether-carboxylic acids of the general formula IV, in which $R^3$, m and q are as defined above, in the form of their alkanolamides and/or alkanolammonium salts with alkanolamines of the general formula II, in which $R^2$ is as defined above, b) fatty acid alkanolamides based on straight-chain or branched, saturated or unsaturated fatty acids having 12 to 22 carbon atoms and amines of the general formula II, c) aryl- and alkylsulphonamidocarboxylic acids of the general formula Va or Vb, in which $R^4$, $R^5$, $R^6$, $R^7$ and $R^8$ are as defined above, in the form of their alkanolamides and/or alkanolammonium salts with alkanolamines of the general formula II, in which $R^2$ is as defined above, d) straight-chain or branched, unsaturated or saturated carboxylic acids having 5 to 22, preferably 5 to 11, carbon atoms to establish a pH in the range from 7.5 to 9.5 or e) straight-chain or branched fatty alcohols having 12 to 18 carbon atoms, are particularly advantageous.

Other particularly advantageous cooling lubricants comprise, as fungicides, pyrithione or derivatives thereof and/or N-alkyldiazenium dioxide salts.

The cooling lubricants can be prepared by mixing the individual components together. If the cooling lubricants are to have a content of fatty acid alkanolamides, it is preferable for the amino esters of the general formula I to be prepared in the manner described above in the form of their mixtures with the fatty acid alkanolamides. This process furthermore offers the advantage that exclusively liquid reaction mixtures are obtained, which can be further processed without extra measures, for example comminution or dissolving in suitable solvents.

The invention is described in more detail below with the aid of particularly preferred embodiment examples.

Examples 1 to 12 show the preparation of derivatives, used according to the invention, of 2,4,6-tris-(omega'-carboxypentylamino)-1,3,5-triazine, called triazinecarboxylic acid for short below, which is commercially obtainable or can be obtained by reaction of cyanuric chloride with the sodium salt of 6-aminohexanoic acid in accordance with EP-B 0 046 139.

The triazinecarboxylic acid can be used as the commercially available product or in the form of the commercially available aqueous product. In the following examples, a solid product containing about 50% by weight of water was employed.

EXAMPLE 1

75 g (0.714 mol) of diethanolamine were stirred with 25 g (0.0267 mol) of triazinecarboxylic acid. After a reaction time of several hours at 150° to 160° C., 10 g of water were distilled off.

The final acid number was 10 mg of KOH/g.

90 g of a clear, medium-viscosity liquid were obtained.

EXAMPLE 2

75 g (1.230 mol) of monoethanolamine were stirred with 25 g (0.0267 mol) of triazinecarboxylic acid at 60° C. and the mixture was heated to 140° to 143° C. After a reaction time of 10 hours, 18 g of water were distilled off.

The final acid number was 12 mg of KOH/g.

A white, solid product was obtained.

EXAMPLE 3

863 g (9.697 mol; 31.5 mol per mol of triazinecarboxylic acid) of 2-amino-1-butanol were stirred with 287 g (0.307 mol) of triazinecarboxylic acid at 60° C. and the mixture was heated to 145° C. After a reaction time of 20 hours, 150 g of water were distilled off.

The final acid number was 10 mg of KOH/g.

1000 g of a clear, low-viscosity liquid were obtained.

EXAMPLE 4

375 g (3.571 mol; 26.7 mol per mol of triazinecarboxylic acid) of 2-(2'-aminoethoxy)-ethanol were stirred with 125 g (0.134 mol) of triazinecarboxylic acid at 60° C. and the mixture was heated to 145° C. After a reaction time of 16 hours, 73 g of water were distilled off.

The final acid number was 7 mg of KOH/g.

427 g of a white, pasty product were obtained.

EXAMPLE 5

228 g (2.171 mol; 7.1 mol per mol of triazinecarboxylic acid) of 2-(2'-aminoethoxy)-ethanol and 627 g (7.045 mol; 23.1 mol per mol of triazinecarboxylic acid) of 2-amino-1-butanol were stirred with 285 g (0.304 mol) of triazinecarboxylic acid at 60° C. and the mixture was heated to 145° C. After a reaction time of 16 hours, 140 g of water were distilled off.

The final acid number was 13 mg of KOH/g.

1000 g of a clear, medium-viscosity liquid were obtained.

EXAMPLE 6

833 g (8.424 mol; 31.5 mol per mol of triazinecarboxylic acid) of AMP 90 were heated to 60° C. and stirred with 250 g (0.267 mol) of triazinecarboxylic acid, and the mixture was heated to 140° to 145° C. After a reaction time of 20 hours, 240 g of water were distilled off.

The final acid number was 15 mg of KOH/g.

843 g of an almost clear, high-viscosity product were obtained.

EXAMPLE 7

990 g (8.319 mol; 23.6 mol per mol of triazinecarboxylic acid) of AEPD were heated to 60° C. and stirred with 330 g (0.353 mol) of triazinecarboxylic acid, and the mixture was heated to 140° to 145° C. After a reaction time of 16 hours, 320 g of water were distilled off.

The final acid number was 10 mg of KOH/g.

1000 g of a clear, high-viscosity liquid were obtained.

EXAMPLE 8

375 g (5.000 mol; 37.4 mol per mol of triazinecarboxylic acid) of monoisopropanolamine were heated to 60° C. and stirred with 125 g (0.134 mol) of triazinecarboxylic acid, and the mixture was heated to 140° C. After a reaction time of 16 hours, 74 g of water were distilled off.

The final acid number was 12 mg of KOH/g.

426 g of a clear, low-viscosity liquid were obtained.

EXAMPLE 9

750 g (5.034 mol; 18.9 mol per mol of triazinecarboxylic acid) of triethanolamine were heated to 60° C. and stirred with 250 g (0.267 mol) of triazinecarboxylic acid, and the mixture was heated to 140° to 145° C. After a reaction time of 16 hours, 130 g of water were distilled off.

The final acid number was 6 mg of KOH/g.

870 g of a clear, medium-viscosity liquid were obtained.

EXAMPLE 10

1st stage 130 g (1.238 mol; 4.8 mol per mol of triazinecarboxylic acid) of 2-(2'-aminoethoxy)-ethanol and 370 g (4.157 mol; 16.2 mol per mol of triazinecarboxylic acid) of 2-amino-1-butanol were reacted with 190 g (0.674 mol; 2.6 mol per mol of triazinecarboxylic acid) of olein at 145° C. After a reaction time of 10 hours, 12 g of water were distilled off.

678 g of a liquid product having an acid number of 7 mg of KOH/g were obtained.

2nd stage 678 g of the liquid from the first stage were heated to 60° C. and stirred with 240 g (0.256 mol) of triazinecarboxylic acid, and the mixture was heated to 140° to 150° C. After a reaction time of 10 hours, 138 g of water were distilled off.

The final acid number was 14 mg of KOH/g.

780 g of a clear, medium-viscosity product were obtained.

EXAMPLE 11

130 g (1.238 mol) of 2-(2'-aminoethoxy)-ethanol, 370 g (4.157 mol) of 2-amino-1-butanol, 174 g (0.497 mol) of sulphonamidocarboxylic acid and 240 g (0.256 mol) of triazinecarboxylic acid were reacted at 145° C. After a reaction time of 12 hours, 143 g of water were distilled off.

771 g of a medium-viscosity, clear, liquid product having a final acid number of 25 mg of KOH/g were obtained.

EXAMPLE 12

130 g (1.238 mol) of 2-(2'-aminoethoxy)-ethanol, 370 g (4.157 mol) of 2-amino-1-butanol, 106 g (0.148 mol) of ether-carboxylic acid and 240 g (0.256 mol) of triazinecarboxylic acid were reacted at 145° C. After a reaction time of 13 hours, 137 g of water were distilled off.

709 g of a clear, medium-viscosity product having a final acid number of 20 mg of KOH/g were obtained.

Comparison Examples 1 to 3 and Examples 13 to 19

A number of the amino esters thus prepared were formulated with water, spindle oil and further additives stated in each case, and in some examples with fungicides, to give mixtures which give cooling lubricants in a dilution with water of 1:20 to 1:80.

Furthermore, mixtures without biocides were formulated in Comparison Examples 1 and 2, and a mixture with a boric acid-alkanolamine condensation product as a biocidal agent were formulated in Comparison Example 3.

Data in % below always relate to parts by weight.

The data in the "Exp." column relate to the explanations of Table 1. All the chemicals listed in Table 1 are commercially obtainable.

Table 1: EXPLANATIONS

1 Tall oil distillate with 25–30% of resin (acid number 155–190)

2 a) isononanoic acid b) 2,2-dimethyl-octanoic acid

3 Spindle oil, viscosity: 22 mm$^2$/s at 40° C.

4 a) Reaction product of 1 mol of chloroacetic acid with a condensation product of 1 mol of a technical-grade oleyl alcohol with 10 mol of ethylene oxide (ether-carboxylic acid)

b) Reaction product of 1 mol of chloroacetic acid with a condensation product of 1 mol of $C_9$- to $C_{13}$ oxo alcohols with 3 mol of ethylene oxide and 2 mol of propylene oxide (ether-carboxylic acid)

5 a) Technical-grade oleyl alcohol (about 90% strength, iodine number about 95)

b) 2-hexyldecanol 6 a) Condensation product of 1 mol of a technical-grade mixture of oleyl and cetyl alcohol with 5 mol of ethylene oxide b) Fatty alcohol polyglycol ether (Emulsogen$^R$ LP)

7 a) Condensation product of 40 parts by weight of diethanolamine with 60 parts by weight of olein b) as a) with addition of 20% of ethanolamine, based on the total amount of condensation product and ethanolamine 8 a) diethylene glycol b) butyldiglycol c) butylglycol 9 a) Sodium petroleumsulphonate having a molecular weight of about 460 b) Sodium alkylbenzenesulphonate having a molecular weight of about 350

10 50% strength potassium hydroxide solution

11 Fungicidal mixture of
10% of the sodium salt of pyrithione
10% of N-(cyclohexyl-diazenium dioxide) potassium hydrate in the form of a 30% strength aqueous solution
10% of propylene glycol
70% of demineralized water 12 Condensation product of 1 mol of boric acid with 3 mol of ethanolamine 13 Arylsulphonamidocarboxylic acid having a molecular weight of about 350 (Hostacor$^R$ H liquid; acid content about 90%, remainder solubilizing agent).

| | Exp. |
|---|---|
| Comparison Example 1 | |
| 7% of fatty acids | 1 |
| 2% of sulphonates | 9b) |
| 5% of fatty acid alkanolamides | 7b) |
| 2% of auxiliaries | 8a) |
| 1% of auxiliaries | 10 |
| 83% of spindle oil | 3 |
| Comparison Example 2 | |
| 8% of fatty acids | 1 |
| 17% of sulphonates | 9a) |
| 4% of fatty acid alkanolamides | 7a) |
| 3% of auxiliaries | 8c) |
| 2% of auxiliaries | 10 |
| 36% of spindle oil | 3 |
| 30% of water | |
| Comparison Example 3 | |
| 20% of boric acid product | 12 |
| 10% of fatty acids | 1 |
| 10% of fatty acid alkanolamides | 7a) |
| 10% of auxiliaries | 8b) |
| 20% of spindle oil | 3 |
| 30% of water | |
| Example 13 | |
| 25% of Example 1 | |
| 31% of spindle oil | 3 |
| 10% of fatty acids | 1 |
| 5% of fatty acids | 2b) |
| 4% of ether-carboxylic acids | 4b) |
| 6% of fatty alcohols | 5a) |
| 14% of water | |
| 5% of non-ionic emulsifiers | 6a) |
| Example 14 | |
| 25% of Example 2 | |
| 31% of spindle oil | 3 |
| 10% of fatty acids | 1 |
| 5% of fatty acids | 2b) |
| 4% of ether-carboxylic acids | 4b) |
| 6% of fatty alcohols | 5a) |
| 5% of non-ionic emulsifiers | 6a) |
| 14% of water | |
| Example 15 | |
| 22% of Example 3 | |
| 11% of fatty acids | 2a) |
| 17% of fatty acids | 1 |
| 6% of ether-carboxylic acids | 4a) |
| 9% of fatty acid alkanolamides | 7a) |
| 4% of fatty alcohols | 5a) |
| 22% of spindle oil | 3 |
| 8% of water | |
| 1% of fungicides | 11 |
| Example 16 | |
| 21% of Example 5 | |
| 21% of fatty acids | 1 |
| 11% of fatty acids | 2a) |
| 7% of ether-carboxylic acids | 4a) |
| 5% of fatty alcohols | 5b) |
| 20% of spindle oil | 3 |
| 13% of water | |
| 2% of fungicides | 11 |
| Example 17 | |
| 25% of Example 7 | |
| 31% of spindle oil | 3 |
| 10% of fatty acids | 1 |
| 3% of fatty acids | 2a) |
| 8% of fatty alcohols | 5a) |
| 5% of non-ionic emulsifiers | 6a) |
| 4% of ether-carboxylic acids | 4b) |
| 1% of fungicides | 11 |
| 13% of water | |
| Example 18 | |
| 25% of Example 8 | |
| 31% of spindle oil | 3 |
| 10% of fatty acids | 1 |
| 5% of fatty acids | 2b) |
| 4% of ether-carboxylic acids | 4b) |
| 6% of fatty alcohols | 5a) |

-continued

|  | Exp. |
|---|---|
| 5% of non-ionic emulsifiers | 6a) |
| 1% of fungicides | 11 |
| 13% of water | |
| Example 19 | |
| 19% of Example 10 | |
| 29% of fatty acids | 1 |
| 29% of spindle oil | 3 |
| 5% of auxiliaries | 8b) |
| 3% of non-ionic emulsifiers | 6b) |
| 1% of fungicides | 11 |
| 14% of water | |
| Example 20 | |
| 23% of Example 11 | |
| 28% of fatty acids | 1 |
| 25% of spindle oil | 3 |
| 5% of non-ionic emulsifiers | 6b) |
| 2% of fatty alcohols | 5b) |
| 2% of auxiliaries | 8b) |
| 1% of fungicides | 11 |
| 14% of water | |
| Example 21 | |
| 23% of Example 12 | |
| 28% of fatty acids | 1 |
| 1% of fatty alcohols | 5a) |
| 4% of non-ionic emulsifiers | 6a) |
| 4% of auxiliaries | 8b) |
| 1% of fungicides | 11 |
| 27% of spindle oil | 3 |
| 12% of water | |

Microbiological Test Method

An inoculation cycle test developed in-house was carried out. For this, the following dilutions of the formulations of Comparison Examples 1 to 3 and of Examples 26 to 42 were prepared with Hamburg town water: 1.25%, 2.5% and 5.0% (corresponds to 1:80, 1:40 and 1:20).

The samples were inoculated several times with a concentrated mixed germ flora. The germ flora contained bacteria, yeasts and fungi from running emulsion systems of varying origin. Their total germ count was about $10^7$ germs/ml.

The amount of mixed germ flora for inoculation of the samples corresponded to six times the amount proposed according to DAB 9 (German Pharmacopoeia). 6 ml of germ flora were used per 100 ml of sample.

The samples were inoculated repeatedly (a maximum of 6 inoculations) by this method (in accordance with K. H. Wallhäusser; Praxis der Sterilisation-Desinfektion-Konservierung-Keimidentifizierung (Practice of Sterilization-Disinfection-Preservation-Germ Identification), 4th edition, Georg Thieme Verlag, Stuttgart 1988), until an antimicrobial action was no longer detectable. From experience, 1 inoculation corresponded to 3 inoculation cycles according to the DAB 9/Wallhäuser method.

This method has the following advantages:

1. A mixed germ flora such as occurs in practice is employed.
2. The samples are exposed to a massive germ loading several times.
3. The method is quick and therefore appropriate for industry. In comparison with the conventional method, which often takes several months, the results are available in a maximum of 8 weeks, if they do not have to be repeated.
4. Conclusions as to the service lives of the emulsions in use in the central systems can be drawn from the results.

The action time of the microorganisms on the samples was about 1 week. After this time, the samples were spread out onto in each case two special nutrient media and incubated. The colony count was then determined under the microscope, and the germ count per ml of sample was determined therefrom. The number of inoculation cycles after which a first germ attack is to be observed is shown in Table 2. This is a measure of the activity of the biocides in the particular samples. The formulations of Examples 13, 14, 15 and 18 based on the compounds of Examples 1, 2, 3 and 8 proved to be particularly active. Example 14 shows a fungicidal action even without addition of pyrithione or derivatives thereof.

TABLE 2

| | Microbiological Results | | | | | | | | | | | |
|---|---|---|---|---|---|---|---|---|---|---|---|---|
| Dilution % | 1.25 | | | | 2.5 | | | | 5 | | | |
| Example | B | Y | F | IC | B | Y | F | IC | B | Y | F | IC |
| Comp. Ex. 1 | | | | | | | | | +++ | ++ | 0 | 3 |
| Comp. Ex. 2 | | | | | | | | | +++ | ++ | 0 | 3 |
| Comp. Ex. 3 | | | | | | | | | 0 | 0 | +++ | 18 |
| 13 | +++ | +++ | 0 | 3 | +++ | 0 | ++ | 12 | 0 | 0 | 0 | 18 |
| 14 | +++ | ++ | 0 | 9 | ++ | ++ | 0 | 12 | + | 0 | 0 | 18 |
| 15 | ++ | ++ | 0 | 3 | ++ | ++ | 0 | 12 | 0 | 0 | 0 | 18 |
| 16 | +++ | 0 | 0 | 3 | +++ | 0 | +++ | 9 | 0 | 0 | 0 | 18 |
| 17 | ++ | ++ | 0 | 3 | + | 0 | 0 | 6 | ++ | + | 0 | 9 |
| 18 | +++ | ++ | 0 | 6 | 0 | 0 | 0 | 18 | 0 | 0 | 0 | 18 |
| 19 | +++ | ++ | 0 | 3 | ++ | ++ | 0 | 3 | + | + | 0 | 15 |

+++ = severe attack - germ count/ml > $10^4$
++ = moderate attack - germ count/ml $10^3$–$10^4$
+ = mild attack - germ count/ml < $10^3$
0 = no attack
B = bacteria
Y = yeasts
F = fungi
IC = first germ attack after x inoculation cycles

We claim:
1. 1,3,5-Triazine-2,4,6-tris-alkyleminocarboxylic acid amino esters and amides of the general formula

$$1,3,5\text{-triazine-2,4,6-tris}[NH-(CH_2)_n-CO-O-R^1] \qquad (I)$$

or $$1,3,5\text{-triazine-2,4,6-tris}[NH-(CH_2)_n-CO-R^{1'}] \qquad (I')$$

in which n denotes a number in the range from 4 to 11 and $R^1$ denotes a C-linked radical of an alkanolamine of the general formula $$(R^2)_3N \qquad (II)$$

and $R^{1'}$ denotes a N-linked radical of an alkanolamine of the general formula $$(R^2)_2N[H] \qquad (II')$$

in which at least one of the groups $R^2$ is a) a hydroxyalkyl group having 2 to 4 carbon atoms, b) a hydroxyalkyl-oxyalkylene group having 4 to 6 carbon atoms or c) a dihydroxyalkyl group having 3 to 6 carbon atoms and, in the case of the general formula II, if less than three of the groups $R^2$ have the above meaning, the other groups $R^2$ are hydrogen, or one of the groups $R^2$ has the abovementioned meanings and the second is an alkyl group having 1 to 6 carbon atoms and the third is hydrogen and, in the case of general formula II', if only one of the groups $R^2$ have the above meaning, the other group $R^2$ is hydrogen, wherein the radical of formula (II) is attached via the carbon atom of the alkyl chain of the alkanolamine group.

2. 1,3,5-Triazine-2,4,6-tris-alkylaminocarboxylic acid amino esters or amides of the general formula I or I', respectively, according to claim 1, in which n denotes the number 5 and $R^1$ and $R^{1'}$ are as defined above.

3. 1,3,5-Triazine-2,4,6-tris-alkylaminocarboxylic acid amino esters or amides of the general formula I or I', respectively, according to claim 1 or 2, in which n is as defined and the radical $R^1$ is derived from primary and secondary alkanolamines of the general formula II.

* * * * *